United States Patent
Wu et al.

(10) Patent No.: US 7,472,789 B2
(45) Date of Patent: Jan. 6, 2009

(54) CONTAINER FOR TRANSPORTING AND PROCESSING THREE-DIMENSIONAL DENTITION MODELS

(75) Inventors: Ken Wu, San Francisco, CA (US); Srinivas Kaza, San Francisco, CA (US); Subir Basu, San Jose, CA (US)

(73) Assignee: Align Technology, Inc., Santa Clara, CA (US)

( * ) Notice: Subject to any disclaimer, the term of this patent is extended or adjusted under 35 U.S.C. 154(b) by 208 days.

(21) Appl. No.: 11/367,737

(22) Filed: Mar. 3, 2006

(65) Prior Publication Data
US 2007/0205116 A1     Sep. 6, 2007

(51) Int. Cl.
*A61B 19/02*      (2006.01)
*B65D 81/02*      (2006.01)
*A61G 15/00*      (2006.01)

(52) U.S. Cl. .................. 206/63.5; 206/523; 433/79; 433/213

(58) Field of Classification Search ............... 206/63.5, 206/83, 523; 433/24, 33–37, 77, 79, 213, 433/215, 60, 214
See application file for complete search history.

(56) References Cited

U.S. PATENT DOCUMENTS

| | | | | |
|---|---|---|---|---|
| 2,860,768 | A * | 11/1958 | Smithers | 206/523 |
| 4,103,424 | A * | 8/1978 | Benjamin et al. | 433/58 |
| 4,294,349 | A * | 10/1981 | Ibsen et al. | 206/63.5 |
| 4,666,037 | A * | 5/1987 | Weissman | 206/63.5 |
| 4,697,700 | A * | 10/1987 | Weissman | 206/83 |
| 4,708,648 | A * | 11/1987 | Weissman | 433/49 |
| 4,763,791 | A * | 8/1988 | Halverson et al. | 206/63.5 |
| 6,767,208 | B2 * | 7/2004 | Kaza | 433/24 |
| 2005/0089815 | A1 * | 4/2005 | Lee | 433/60 |
| 2006/0175272 | A1 * | 8/2006 | Wen | 211/70.6 |

* cited by examiner

*Primary Examiner*—Bryon P Gehman
(74) *Attorney, Agent, or Firm*—Klein, O'Neill & Singh, LLP

(57) ABSTRACT

A method of transporting and processing a set of three-dimensional dentition models includes (a) providing a container having an outer shell containing a shock-absorbing core, wherein the core defines a plurality of compartments each configured to hold one model in the set of three-dimensional dentition models; (b) loading each of the dentition models into its respective compartment; (c) transporting the container to a processing site; and (d) processing the dentition models while they are in the container.

18 Claims, 4 Drawing Sheets

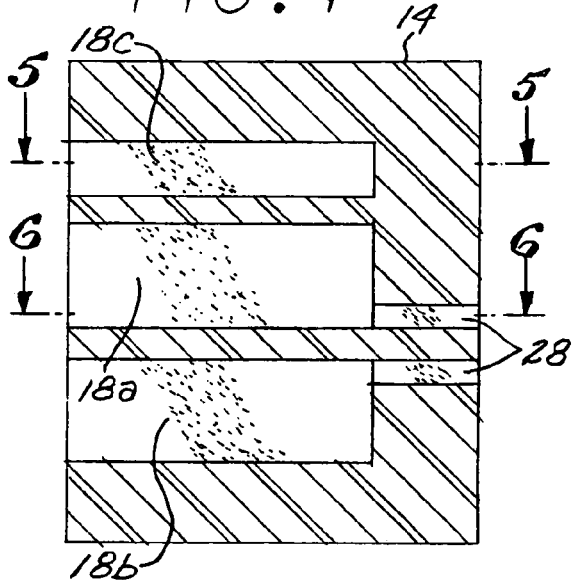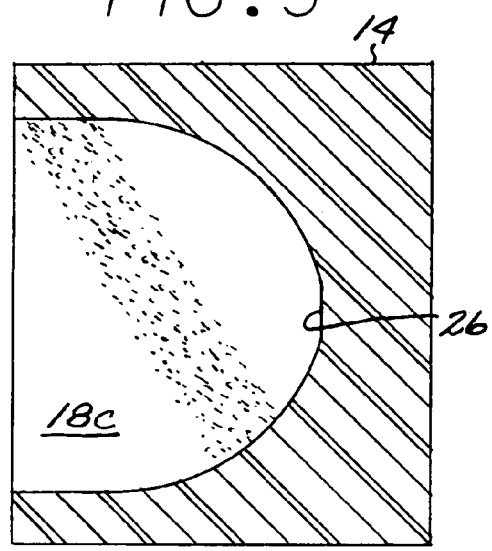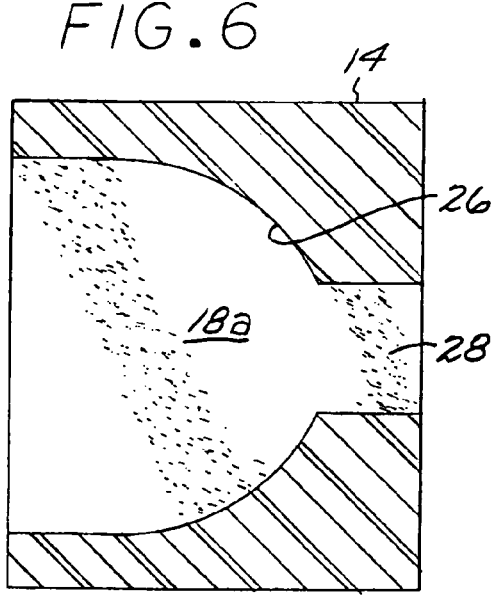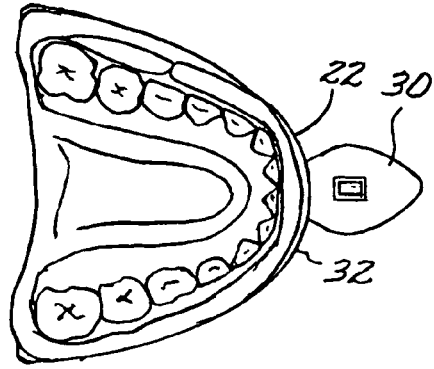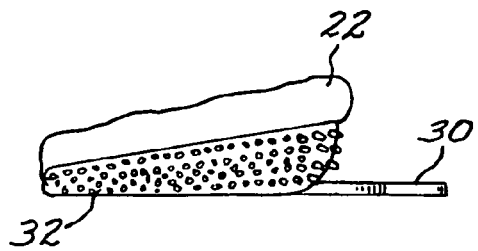

ABLE FOR TRANSPORTING AND
PROCESSING THREE-DIMENSIONAL
DENTITION MODELS

CROSS-REFERENCE TO RELATED
APPLICATIONS

Not Applicable

FEDERALLY-SPONSORED RESEARCH AND
DEVELOPMENT

Not Applicable

BACKGROUND OF THE INVENTION

This invention relates, in a first aspect, to the field of containers for transporting and storing three-dimensional dentition models (dental casts and impressions). In a second aspect, the present invention relates to a method of shipping three-dimensional dentition models to a processing facility and for handling the models at the facility.

In dentistry, and particularly in the field of orthodontics, it is frequently necessary to create a "stone" model or cast that is an accurate replica of the hard and soft tissues (i.e, teeth and gums) of a patient's dental arch. The first step in making the stone model is to make a dental impression, using an impression material. Typical impression materials include alginate (irreversible hydrocolloid), agar (reversible hydrocolloid), polysulfide, polyether, and polyvinylsiloxane (PVS). Impression materials are generally transferred to the patient's mouth in an impression tray while the materials are initially fluid and require support. Once the tray is positioned on the patient's dental arch, the materials undergo setting by either a chemical or physical process. After setting, the impression is removed from the patient's mouth, and a stone model may then be prepared, using a dental gypsum material that is initially fluid and that can be poured into the impression, where it hardens to form a rigid replica of the dental arch. This rigid replica is called a cast or a stone.

State-of-the-art processes for the fabrication of orthodontic appliances are directed toward the production of a set of appliances that are custom-made for each individual patient, and that are designed to be used in a pre-defined sequence to move the patient's teeth progressively toward a predetermined final orthodontic arrangement. The fabrication process starts with a dentist making impressions of the upper and lower dental arch. A stone or cast may also be made from the upper and lower impressions, respectively. A "bite registration," an impression of the upper and lower teeth together as they are mutually registered when the patient bites, is also typically made. For the purpose of the ensuing description, the impressions, the stones, and the bite registration may be collectively referred to as 3-D dentition models. For each patient, the 3-D dentition models (a bite registration and upper and lower dental arch models, the dental arch models being either impressions or stones), are packed by the dentist and shipped to an orthodontic appliance manufacturing facility in a shipping container. The 3-D dentition models are then removed from the shipping container. Impressions and bite registrations (but not stones) must then be disinfected. In some cases the models are then loaded into a specially designed carrier or holder in which they are held while they undergo a scanning procedure, typically by means of a CT scanning device. After scanning, the dentition models are unloaded from the scanning carrier or holder and stored in an archive area. A dentist may also wish to send the stones/impressions and/or bite registration to a lab or other facility for other purposes, such as having a digital image prepared for diagnostic or other uses.

The above process thus entails three separate, labor-intensive steps after receipt of the stones and the bite registration by the appliance manufacturing facility:

1. Removing the dentition models from the shipping container;
2. Loading the dentition models into a scanning carrier or holder before scanning is performed; and
3. Unloading the dentition models from the carrier or holder after the scanning is completed.

In addition, for dentition models that are impressions or bite registrations, a disinfecting step must be performed between the step of removing the dentition models from the container and the step of loading them into a scanning carrier or holder.

It can be seen that the above procedure requires the 3-D dentition models to be manually handled, which is time-consuming, and which can result in increased opportunities for the dentition models to be damaged. It would thus be greatly advantageous to simplify the above procedure and to make it less labor-intensive and thus less costly and time-consuming. It would also be advantageous to reduce the risk of damage to the dentition models from the time of receipt by the manufacturing facility through completion of the scanning procedure.

SUMMARY OF THE INVENTION

Broadly, the present invention, in a first aspect, is a container for use in transporting, scanning, and storing a set of 3-D dentition models for a patient, comprising an outer container shell and an inner shock-absorbing core, wherein the inner core is provided with first and second compartments respectively configured to receive and hold upper and lower dental arch models, which may be stones or impressions. The core may advantageously be provided with a third compartment configured to receive and hold a bite registration. In a preferred embodiment, the shell is configured as a cubic box made of durable cardboard, while the core has a cubic outer configuration dimensioned to conform to the interior of the outer shell or box. The core is preferably made of a cushioning polymeric foam, such as, for example, polyethylene or polyurethane, or any suitable equivalent. Alternatively, the core may be made of a relatively soft cardboard, such as that used for egg cartons.

In applications in which the container is used to hold the dentition models for scanning, the shell and the core must be made of materials that are transparent to the scanning radiation. For example, where the scanning is performed with X-rays (e.g., CT scanning), the shell may be either cardboard or a low-density (or thin) plastic, while any of the above-mentioned polymeric foams, if of suitably low density, would be acceptable for the core material, as would be a soft cardboard.

In another aspect, the present invention is a method of transporting a set of 3-D dentition models, wherein the set of 3-D dentition models comprises at least an upper dental arch model (stone or impression) and a lower dental arch model (stone or impression), the method comprising the steps of (a) providing a container comprising an outer shell and an inner shock-absorbing core configured to hold the upper and lower dental arch models in first and second compartments, respectively; (b) loading the upper dental arch model and the lower dental arch model into the first and second compartments, respectively; and (c) transporting the container to a remote processing (scanning and/or manufacturing) site. The method may also include either or both of the steps of scanning the upper and lower dental arch models with a scanning apparatus while they are contained in the container, and storing the container with the upper and lower dental arch models contained in it after it is received at the processing site.

In a specific preferred embodiment, the dentition model set includes an upper dental arch model (stone or impression), a lower dental arch model (stone or impression), and a bite registration. The container core in this embodiment is configured to hold the upper dental arch model, the lower dental arch model, and the bite registration, in first, second and third compartments, respectively. The loading step is defined as the step of loading the upper dental arch model, the lower dental arch model, and the bite registration into the first, second, and third compartments, respectively. In this preferred embodiment, the step of transporting the container is followed by the steps of (d) scanning the upper and lower dental arch models and the bite registration with a scanning apparatus while they are contained in the container; and (e) removing the container with the upper and lower dental arch models and the bite registration from the scanning apparatus for transport to a storage site or for disposal.

It is understood that the invention, in both of the aspects summarized above, may be practiced with or without a bite registration. If the invention is practiced without a bite registration, the container may be made with only first and second compartments, i.e., for the upper and lower dental arch models, respectively. More practically, however, and preferably, a three-compartment container will be used, and with the bite registration compartment (i.e., the "third compartment" specified above) being left empty if no bite registration is included in the dentition model set.

As will be more fully appreciated from the detailed description of the invention that follows, the present invention provides a safe and economical mechanism for transporting the dentition model set, for securing these items for scanning or other processing at a processing site, and for post-processing storage of these items. The need for a separate shipping container and a scanning or processing carrier is eliminated, as is the need to handle the dentition models for removal from the shipping container, loading them into a scanning or processing carrier, and unloading them from the scanning or processing carrier. Furthermore, the costly and time-consuming step of disinfecting dental impressions and bite registrations before loading them into the scanning or processing carrier is eliminated. Accordingly, a great deal of time and expense is saved by eliminating several labor-intensive steps, while the opportunities for breakage are minimized.

BRIEF DESCRIPTION OF THE DRAWINGS

FIG. 4 is a cross-sectional view taken along line 4-4 of FIG. 2;

FIG. 5 is a cross-sectional view taken along line 5-5 of FIG. 4;

FIG. 6 is a cross-sectional view taken along line 6-6 of FIG. 4;

FIG. 7 is a top plan view of a typical upper impression and its associated impression tray, of the type that would be placed in the container of FIG. 1;

FIG. 8 is a side elevational view of the upper impression and impression tray of FIG. 7;

DETAILED DESCRIPTION OF THE INVENTION

Referring first to FIGS. 1-6, a container 10 for three-dimensional dentition models, in accordance with a preferred embodiment of the present invention, comprises an outer box or shell 12 and an inner foam core 14. The outer shell 12 is preferably of a durable cardboard, preferably with a moisture-resistant coating, such as is commonly used for shipping boxes. A rigid or semi-rigid polymer may also be used. The configuration of the shell 12 is preferably cubic or approximately cubic, but it may be a rectangular hexahedron, or any other convenient shape. The shell 12 is closed on the top, the two opposed sides, and the back end, with an open front end that is closable by a flap 16 attached to one side (as shown), or alternatively to the top or bottom.

Figure 10:
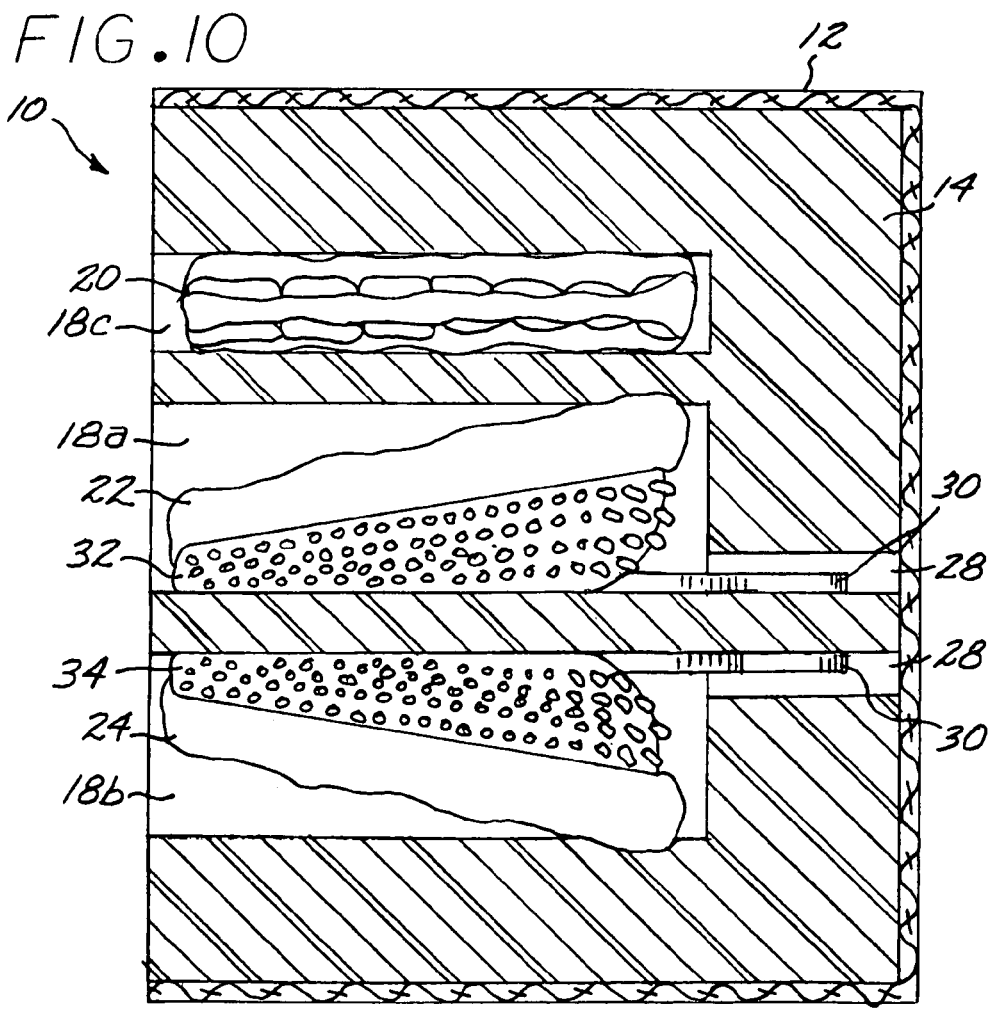
FIG. 10 shows the container of the present invention, in cross-section, with a bite registration, upper impression and tray, and lower impression and tray (all shown in side elevation) installed in their respective compartments.
Figure 11:
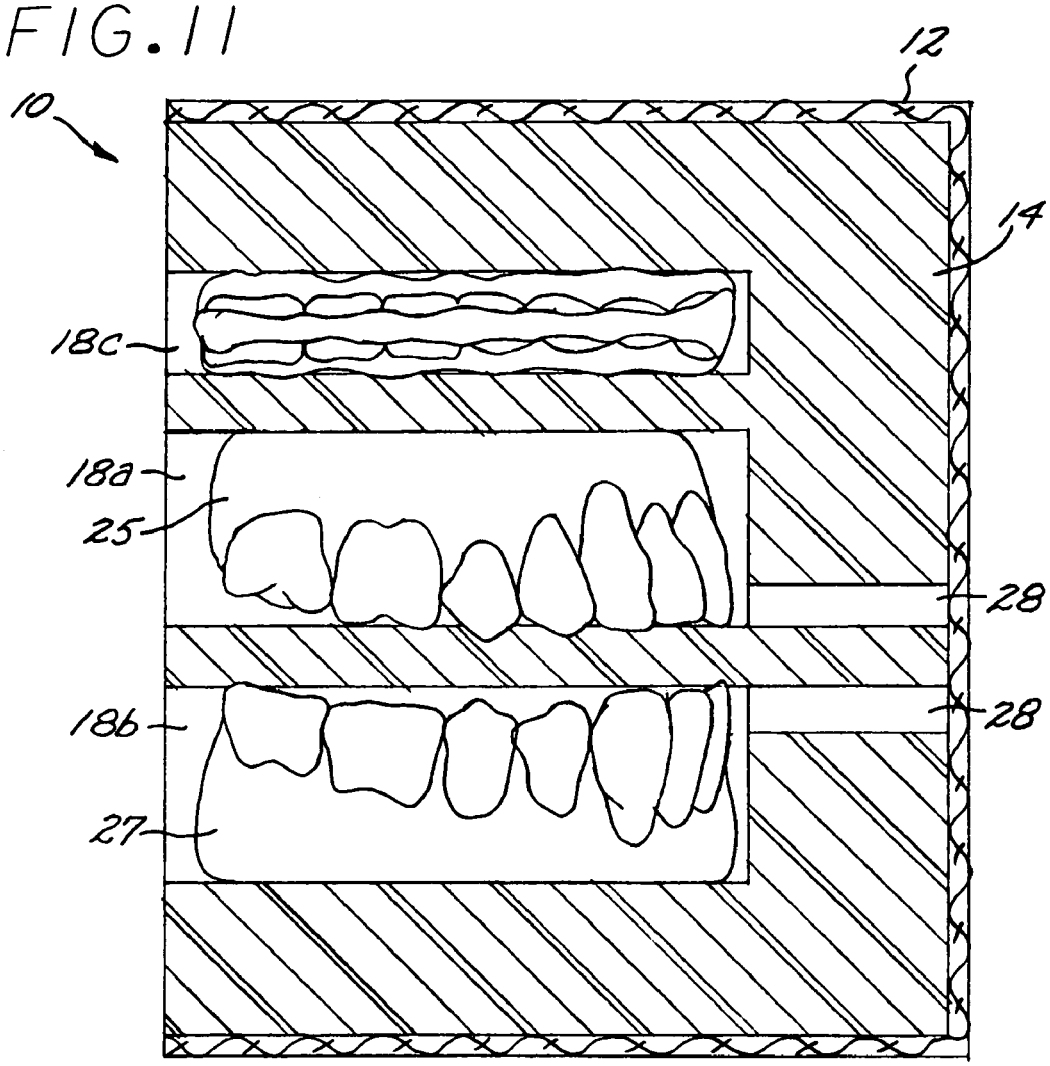
FIG. 11 is a view similar to that of FIG. 10, but showing the container of the present invention, in cross-section, with a bite registration, an upper stone, and a lower stone (all in side elevation) in their respective compartments.

The core 14 is preferably made of a shock-absorbing polymeric foam, such as, for example, polyethylene or polyurethane, or any suitable equivalent. Alternatively, the core 14 may be made of a soft cardboard, of the type used, for example, to make egg cartons. With an outer configuration conforming in shape and size to the interior dimensions of the shell 12, the core 14 can be slipped into the interior of the shell 12 with a snug fit. The core 14 is formed with first, second, and third front-opening compartments, designated 18a, 18b, 18c, respectively that are dimensioned to receive the dentition models in a dentition model set. Specifically, the first and second compartments 18a, 18b are dimensioned to receive, respectively, upper and lower dental arch models, which may be upper and lower impressions 22, 24 (FIGS. 7-10) or upper and lower stones 25, 27 (FIG. 11). The third compartment 18c is dimensioned to receive a bite registration 20 (FIGS. 10 and 11), as discussed below. Thus, each of the compartments 18a, 18b, 18c may advantageously be configured with an arcuate rear wall 26, as shown in FIGS. 5 and 6, which conforms generally to the configuration of the dentition model it is to contain.

Figure 1:
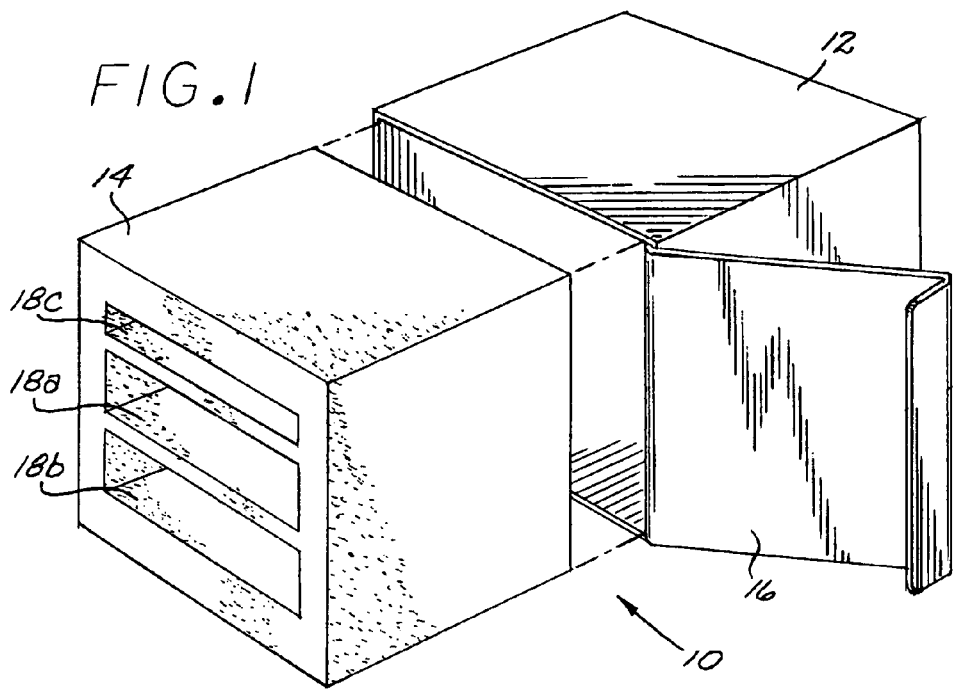
FIG. 1 is a perspective view of a dentition model container in accordance with a preferred embodiment of the invention, showing the inner foam core and the outer shell before installation of the former into the latter.
Figure 2:
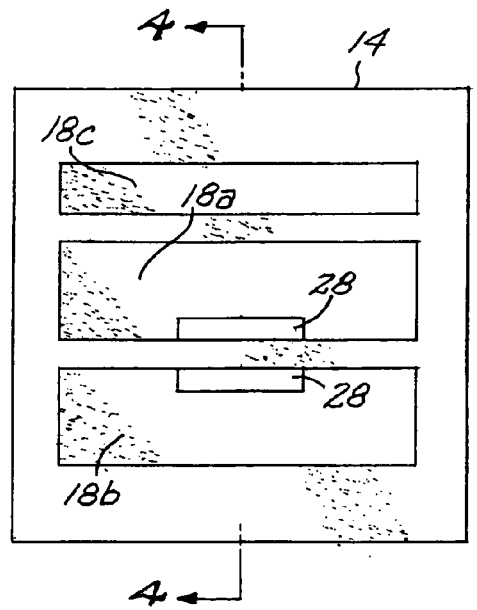
FIG. 2 is front elevational view of the foam core of a container in accordance with a preferred embodiment of the invention.
Figure 3:
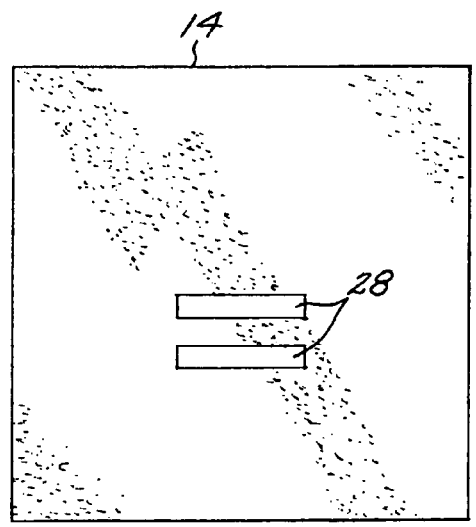
FIG. 3 is a rear view of the foam core of a container in accordance with a preferred embodiment of the invention.

As shown in FIGS. 3 and 4, a slot 28 is advantageously formed in the rear wall 26 of each of the first and second compartments 18a, 18b, to accommodate and receive a holder or tab 30 that may extend forwardly from the front of an upper impression tray 32 (FIGS. 7 and 8) and from the front of a lower impression tray 34, which respectively hold an upper impression 22 and a lower impression 24 in accordance with conventional techniques for forming the impressions.

Figure 9:
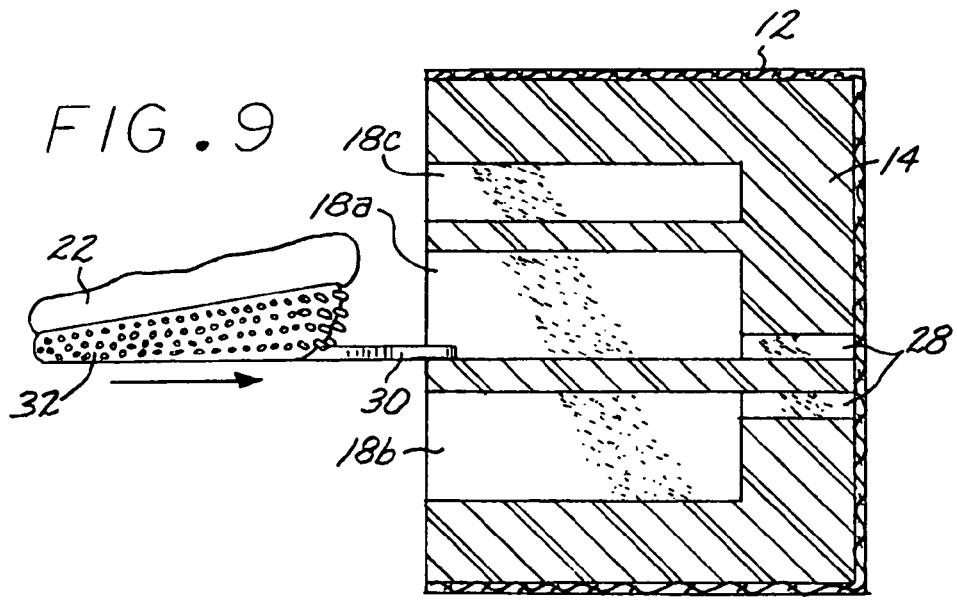
FIG. 9 shows the installation of the upper impression and tray of FIGS. 7 and 8, in side elevation, into the associated compartment in the container of the present invention, shown in cross-section.

FIGS. 7 and 8, show an upper impression 22. The upper impression 22 (like the lower impression 24 shown in FIG. 10) is typically made of alginate or polyvinylsiloxane (PVS). As mentioned above, the upper impression 22 is typically formed in and contained in an upper impression tray 32 having a tray holder or tab 30 extending forwardly from its front end. FIG. 9 shows how the upper impression 22 is inserted into the associated first compartment 18a, so that the tray holder or tab 30 fits into the slot 28 in the rear compartment wall 26. Likewise, as shown in FIG. 10, the lower impression 24 is similarly inserted into its associated second compartment 18b, and the bite registration 20 is similarly inserted into its associated third compartment 18c. After the upper and lower impressions 22, 24 and the bite registration 20 are loaded into their associated compartments, the container 10 is closed by closing the flap 16 (FIG. 1), and it is sealed by conventional sealing means (such as tape or adhesive, not shown) for transport to a remote processing facility, such as an orthodontic appliance manufacturing facility. At the facility, the dentition models are processed as appropriate. Specifically, for example, if the facility is an orthodontic appliance or dental prosthesis manufacturing facility, the dentition models may be scanned while still in the container 10, by state-of-the-art scanning techniques (such as CT scanning). The container 10, with the dentition models contained within it, may then be moved to a storage or archive location FIG. 11 is similar to FIG. 10, but it shows the dental arch models as comprising an upper stone 25 placed in the first compartment 18a and a lower stone 27 placed in the second compartment 18b. As in FIG. 10, a bite registration 20 is placed in the third compartment 18c. As described above with respect to FIG. 10, the container 10 is sealed for transport to a remote processing facility, such as an orthodontic appliance manufacturing facility. At the facility, the stones 25, 27 and the bite registration 20 may be scanned while still in the container 20, or they may be processed in other ways for the manufacture of orthodontic appliances, dental prostheses, etc. As mentioned above, the container 10 may then be used for storing and/or archiving the dentition models contained within it.

Figure 12:
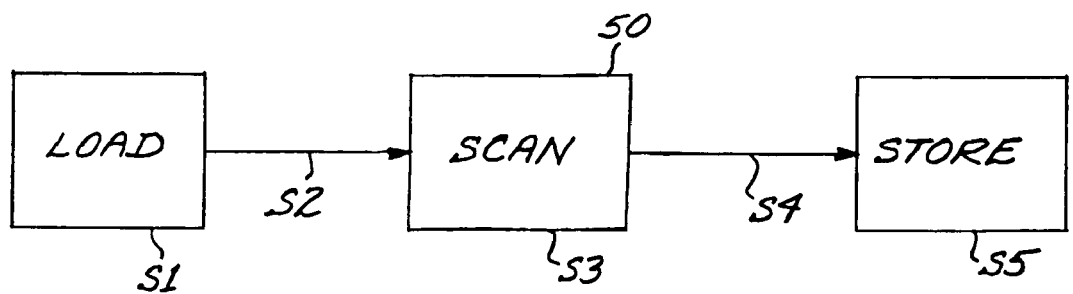
FIG. 12 is a schematic diagram illustrating the steps of transporting, scanning, and storing a set of 3-D dentition models in accordance with the method of the present invention.

FIG. 12 shows diagrammatically the steps in a preferred embodiment of a method of handling a set of dentition models (i.e., a bite registration 20 and upper and lower dental arch models, the dental arch models comprising upper and lower impressions 22, 24, or upper and lower stones 25, 27) in accordance with the present invention, Specifically, the 3-D dentition models are loaded into the container 10 in accordance with the present invention, as described above, and as shown schematically as step S1 in FIG. 12. The container 10 is closed and sealed, as described above, and then transported to a remote processing facility (step S2). At the remote processing facility, the dentition models, still contained in the closed container 10, may be scanned by a scanning apparatus 50 (step S3) or otherwise processed. The container 10, with the dentition models still inside it, is removed from the processing or scanning apparatus 50 (step S4), and it may then be sent to a storage facility or archive (step S5), or otherwise disposed of. The dentition models need never be removed from or handled throughout the process, from transportation to the manufacturing facility, through scanning and storage or disposal.

From the foregoing, it can be seen that the present invention greatly simplifies the handling of the dentition models, and, by eliminating several labor-intensive steps, it reduces the cost and time for processing the models through scanning and into post-scanning storage. Furthermore, by eliminating the handling of the dentition models outside of a closed, shock-absorbing container, the likelihood of damage to the models is minimized.

While a preferred embodiment of the invention has been described above and illustrated in the drawings, it is understood that this embodiment is exemplary only as the currently preferred embodiment of the invention. As mentioned above, the configuration of the various components (such as the shell 12, the core 14, and the compartments 18a, 18b, 18c) may be varied to suit different needs and applications. For example, the core 14 may be made with just two compartments, one for the upper impression or stone, and the other for the lower impression or stone, for applications in which a bite registration is not needed. Likewise, suitable equivalents for the specific materials mentioned above (such as for the shell 12 and the core 14) may suggest themselves to those skilled in the pertinent arts. These materials must be suitable for whatever processing is performed in step S3 of the method illustrated in FIG. 12. For example, if CT scanning is to be preformed, the materials must be transparent to X-rays. If the processing includes irradiation or scanning by other mechanisms, the materials must be appropriate for use with such mechanisms. If no scanning or irradiation is to be employed, then it may be desirable to optimize the materials for protecting the dentition models during transport and/or storage. These variations and modifications, as well as others that may suggest themselves, are deemed to be within the spirit and scope of the present invention, as defined in the claims that follow.

What is claimed is:

1. A method of transporting and processing a set of three-dimensional dentition models, wherein the set includes an upper dental arch model and a lower dental arch model, the method comprising the steps of:
   (a) providing a container comprising an outer shell and an inner shock-absorbing core configured to hold the upper dental arch model and the lower dental arch model in separate compartments fixed relative to each other within the core;
   (b) loading the upper dental arch model and the lower dental arch model into their respective separate compartments;
   (c) transporting the container to remote processing site; and
   (d) processing the upper and lower dental arch models while they are contained in the container.

2. The method of claim 1, further comprising the step of (e) storing the container with the upper and lower dental arch models contained within it.

3. The method of claim 1, wherein the set of dentition models further includes a bite registration; wherein the core is configured to hold the bite registration, the upper dental arch model, and the lower dental arch model in separate compartments; wherein the loading step further includes the loading of the bite registration into one of the separate compartments; and wherein the processing step includes the processing of the bite registration, the upper dental arch model, and the lower dental arch model while they are contained in the container.

4. The method of claim 3, further comprising the step of storing the container with the upper and lower dental arch models and the bite registration contained within it.

5. The method of claim 3, wherein the processing step includes the step of scanning the upper and lower dental arch models and the bite registration with a scanning radiation while they are contained within the container.

6. The method of claim 1, wherein the processing step includes the step of scanning the upper and lower dental arch models with a scanning radiation while they are contained within the container.

7. A method of transporting and processing a set of three-dimensional dentition models, the method comprising the steps of:
  (a) providing a container comprising an outer shell and an inner shock-absorbing core defining a plurality of compartments, wherein the compartments are fixed relative to each other within the core, and wherein each of the compartments is configured to hold one model in the set of dentition models;
  (b) loading each of the dentition models into its respective compartment;
  (c) transporting the container to a remote processing site; and
  (d) processing the dentition models while they are contained in the container.

8. The method of claim 7, further comprising the step of (e) storing the containers with the dentition models contained within it.

9. The method of claim 7, wherein the processing step includes the step of scanning the dentition models with a scanning radiation while they are contained within the container.

10. A method of transporting and processing a set of three-dimensional dentition models, wherein the set includes an upper dental arch model and a lower dental arch model, the method comprising the steps of:
  (a) providing a container comprising an outer shell and an inner core configured to hold the upper dental arch model and the lower dental arch model in separate compartments, wherein the core is made from a material selected from the group consisting of polymeric foam and soft cardboard;
  (b) loading the upper dental arch model and the lower dental arch model into their respective separate compartments;
  (c) transporting the container to a remote processing site; and
  (d) processing the upper and lower dental arch models while they are contained in the container.

11. The method of claim 10, further comprising the step of (e) storing the container with the upper and lower dental arch models contained within it.

12. The method of claim 10, wherein the set of dentition models further includes a bite registration; wherein the core is configured to hold the bite registration, the upper dental arch model, and the lower dental arch model in separate compartments; wherein the loading step further includes the loading of the bite registration into one of the separate compartments; and wherein the processing step includes the processing of the bite registration, the upper dental arch model, and the lower dental arch model while they are contained in the container.

13. The method of claim 12, further comprising the step of storing the container with the upper and lower dental arch models and the bite registration contained within it.

14. The method of claim 12, wherein the processing step includes the step of scanning the upper and lower dental arch models and the bite registration with a scanning radiation while they are contained within the container.

15. The method of claim 10, wherein the processing step includes the step of scanning the upper and lower dental arch models with a scanning radiation while they are contained within the container.

16. A method of transporting and processing a set of three-dimensional dentition models, the method comprising the steps of:
  (a) providing a container comprising an outer shell and an inner core defining a plurality of compartments, wherein each of the compartments is configured to hold one model in the set of dentition models, and wherein the core is made of a material selected from the group consisting of polymeric foam and soft cardboard;
  (b) loading each of the dentition models into its respective compartment;
  (c) transporting the container to a remote processing site; and
  (d) processing the dentition models while they are contained in the container.

17. The method of claim 16, further comprising the step of (e) storing the container with the dentition models contained within it.

18. The method of claim 16, wherein the processing step includes the step of scanning the dentition models with a scanning radiation while they are contained within the container.

* * * * *

UNITED STATES PATENT AND TRADEMARK OFFICE
CERTIFICATE OF CORRECTION

PATENT NO. : 7,472,789 B2  Page 1 of 1
APPLICATION NO. : 11/367737
DATED : January 6, 2009
INVENTOR(S) : Ken Y. K. Wu et al.

It is certified that error appears in the above-identified patent and that said Letters Patent is hereby corrected as shown below:

In column 5, line 47, delete "invention, Specifically," and insert -- invention. Specifically, --, therefor.

In column 6, line 44, in Claim 1, after "to" insert -- a --.

In column 7, line 1, in Claim 6, delete "claim 1," and insert -- claim 3, --, therefor.

Signed and Sealed this

Eighth Day of December, 2009

David J. Kappos
*Director of the United States Patent and Trademark Office*